(12) United States Patent
Sumikawa et al.

(10) Patent No.: US 10,089,422 B2
(45) Date of Patent: Oct. 2, 2018

(54) STRESS-STRAIN RELATION SIMULATION METHOD, SPRINGBACK-AMOUNT PREDICTION METHOD, AND SPRINGBACK ANALYZER

(71) Applicant: JFE STEEL CORPORATION, Tokyo (JP)

(72) Inventors: Satoshi Sumikawa, Tokyo (JP); Akinobu Ishiwatari, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 370 days.

(21) Appl. No.: 14/765,208

(22) PCT Filed: Feb. 10, 2014

(86) PCT No.: PCT/JP2014/053069
§ 371 (c)(1),
(2) Date: Jul. 31, 2015

(87) PCT Pub. No.: WO2014/141794
PCT Pub. Date: Sep. 18, 2014

(65) Prior Publication Data
US 2015/0370936 A1 Dec. 24, 2015

(30) Foreign Application Priority Data
Mar. 14, 2013 (JP) .................. 2013-051385

(51) Int. Cl.
*G06F 17/50* (2006.01)
*G01N 3/08* (2006.01)
(Continued)

(52) U.S. Cl.
CPC .......... *G06F 17/5009* (2013.01); *G01N 3/08* (2013.01); *G01N 33/442* (2013.01); *G06F 17/16* (2013.01);
(Continued)

(58) Field of Classification Search
None
See application file for complete search history.

(56) References Cited

U.S. PATENT DOCUMENTS 6,009,378 A * 12/1999 Tang .................. B21D 37/20
700/127
7,058,618 B2 * 6/2006 Loosen ................ G01N 3/08
706/16

(Continued)

FOREIGN PATENT DOCUMENTS

| CN | 201548449 U | 8/2010 |
| JP | 2003194686 A | 7/2003 |
| JP | 3809374 B2 | 8/2006 |

OTHER PUBLICATIONS

Li, K. P., W. P. Carden, and R. H. Wagoner. "Simulation of springback." International Journal of Mechanical Sciences 44.1 (2002): 103-122.*

(Continued)

*Primary Examiner* — Aniss Chad
*Assistant Examiner* — Nithya J Moll
(74) *Attorney, Agent, or Firm* — Oliff PLC

(57) ABSTRACT

Displacement or a load is applied to an elastic-plastic material to deform the elastic-plastic material plastically to acquire experimental values of a stress-strain relation. With a kinematic-hardening incremental vector $d\alpha_{ij}$ of a yield surface in an elastic-plastic constitutive model as a predetermined first equation, the elastic-plastic constitutive model being defined as a function of stress and back stress, a computer identifies material constants contained in the elastic-plastic constitutive model with the acquired experimental values. The computer identifies material constants contained in a predetermined second equation on the basis of the acquired experimental values and the predetermined first equation into which the identified material constants are (Continued)

substituted. The computer simulates the stress-strain relation of the elastic-plastic material with the predetermined first equation, the predetermined second equation, and the elastic-plastic constitutive model into which the identified material constants are substituted.

6 Claims, 10 Drawing Sheets

(51) Int. Cl.
    *G01N 33/44* (2006.01)
    *G06F 17/16* (2006.01)
    *B21D 22/00* (2006.01)

(52) U.S. Cl.
    CPC ...... *B21D 22/00* (2013.01); *G01N 2203/0075* (2013.01); *G01N 2203/0092* (2013.01)

(56) References Cited

U.S. PATENT DOCUMENTS

| | | | | |
|---|---|---|---|---|
| 2002/0065613 A1* | 5/2002 | Woods | ............... | G01N 33/442 702/42 |
| 2002/0077795 A1* | 6/2002 | Woods | ............... | G01N 3/10 703/6 |
| 2002/0157478 A1* | 10/2002 | Seale | ............... | G01N 3/00 73/789 |
| 2003/0216894 A1* | 11/2003 | Ghaboussi | ............... | E02D 1/022 703/2 |
| 2003/0222871 A1* | 12/2003 | Brombolich | ............... | G06F 17/5018 345/427 |
| 2013/0238301 A1* | 9/2013 | Kaushik | ............... | G06Q 10/04 703/6 |

OTHER PUBLICATIONS

Yoshida, Fusahito, and Takeshi Uemori. "A model of large-strain cyclic plasticity and its application to springback simulation." International Journal of Mechanical Sciences 45.10 (2003): 1687-1702.*

Li, Xuechun, et al. "Effect of the material-hardening mode on the springback simulation accuracy of V-free bending." Journal of Materials Processing Technology 123.2 (2002): 209-211.*

Feb. 29, 2016 Extended Search Report issued in European Patent Application No. 14765635.9.

Eggertsen, P.A. et al.; "On Constitutive Modeling for Springback Analysis," International Journal of Mechanical Sciences (2010),vol. 52, No. 6,pp. 804-818.

Kessler, L. et al., "Springback Simulation with Complex Hardening Material Models," (2008), pp. 1-10.

Eggertsen, Per-Anders et al., "On the Identification of Kinematic Hardening Material Parameters for Accurate Springback Predictions," International Journal of Material Forming: Official Journal of the European Scientific Assocaition for Material Forming (2010) vol. 4, No. 2, pp. 103-120.

Dec. 6, 2016 Office Action issued in Chinese Patent Application No. 201480013384.9.

Ma Nilngxu et al. "Springback Prediction by Yoshida-Uemori Model and Compensation of Tool Surface Using JSTAMP". (2011) pp. 1-6.

Yoshida, Fusahito et al., "A Model of Large-Strain Cyclic Plasticity Describing the Bauschinger Effect and Workhardening Stagnation," International Journal of Plasticity, vol. 18, (2002), pp. 661-686.

Apr. 15, 2014 Search Report issued in International Patent Application No. PCT/JP2014/053069.

* cited by examiner

STRESS-STRAIN RELATION SIMULATION METHOD, SPRINGBACK-AMOUNT PREDICTION METHOD, AND SPRINGBACK ANALYZER

FIELD

The present invention relates to a stress-strain relation simulation method for evaluating a stress-strain relation of an elastic-plastic material, a springback-amount prediction method for predicting the amount of springback of the elastic-plastic material during press forming, and a springback analyzer for a press-formed product.

BACKGROUND

Press forming is a processing method in which a die is pressed onto a blank (metal sheet) to be formed, whereby the shape of the die is transferred to the blank. In this press forming, what is called springback may occur in which the blank having been deformed slightly recovers after a press-formed product is removed from the die, which may make the shape of the press-formed product different from the desired shape. Accordingly, in the press forming, it is necessary to predict the amount of springback of the press-formed product and to design the shaped of the die so that the shape of the press-formed product after the springback becomes the desired shape on the basis of the prediction result.

The springback due to removal of stress applied in the processing occurs when the press-formed product is removed from the die. The springback will be described in more detail with reference to FIG. 16. FIG. 16 is a diagram illustrating a relation between strain and stress applied onto a material in a press-forming process and in a springback process, with strain on the horizontal axis and stress on the vertical axis. As depicted in FIG. 16, when an external force a is applied onto the material in the press-forming process, after the material undergoes the elastic deformation region, plastic deformation occurs starting at the yield point A, and the plastic deformation continues to the point B where the strain amount $\varepsilon_2$ (stress $\sigma_2$) corresponds to the desired shape. When the material is removed from the die, the external force is unloaded and the stress a decreases. This unloading ends at the point C where forces acting on the entire material are balanced with the strain amount $\varepsilon_1$ (stress $\sigma_1$).

The amount of springback is determined by the difference in the strain amount $\varepsilon$ generated in this unloading process, i.e., the difference $\Delta\varepsilon$ between the strain amount $\varepsilon_2$ at the unloading-start point B and the strain amount $\varepsilon_1$ at the unloading-end point C. In a classic mathematical model called a conventional isotropic-hardening model, because it is assumed that the region from the unloading-start point B to the point D where the absolute value of the stress $\sigma_2$ is equal to that of the unloading start point B is in an elastic deformation region, in other words, a region in which the relation between stress and strain is linear, the unloading-end point should be the point E. However, in many actual materials, such a linear region hardly exist in the unloading process and a yield phenomenon occurs much earlier than the point D, deviating from the elastic deformation region, so that the relation between stress and strain (stress-strain relation) represents a non-linear curve.

Such an early yield phenomenon after the stress reversal is called Bauschinger effect. To reproduce the Bauschinger effect, kinematic hardening needs to be considered. The kinematic hardening means hardening with a yield surface moving without changing its area. Representative examples considering the kinematic hardening include Yoshida-Uemori model (see Non Patent Literature 1). The Yoshida-Uemori model can reproduce the Bauschinger effect. Furthermore, in the Yoshida-Uemori model, the non-linear stress-strain relation immediately after the stress reversal is linearly approximated as an apparent gradient of stress versus strain (apparent Young's modulus) on the assumption that work hardening occurs linearly.

However, the behavior of the non-linear stress-strain relation in the unloading process is apparently different from the behavior obtained by linearly approximating this relation, and thus the stress-strain relation cannot be accurately reproduced by the Yoshida-Uemori model. In view of such a background, Patent Literature 1 describes a method for expressing the Bauschinger effect that occurs in an initial stage of the unloading process. In this method, the stress at the beginning of plastic deformation in the unloading process is identified based on the stress-strain gradient to make the stress at the yield point A (yield stress) lower than that in a conventional technique. Specifically, in this technique, the Bauschinger effect that occurs in an initial stage of the unloading process is expressed by reducing the elastic region in which the stress-strain relation is linear and increasing the non-linear work-hardening region.

In the method described in Patent Literature 1, to improve the accuracy in the work-hardening (plastic-deformation) region after yielding again during the unloading, a coefficient (or parameter) of saturation speed of kinematic hardening of a yield surface is defined as a function of equivalent plastic strain. This method assumes that, in the stress-strain gradient, the saturation speed is high when the stress rapidly increases in a region where the strain is small, and the saturation speed is low when the strain is high and the stress does not increase so much.

CITATION LIST

Patent Literature

Patent Literature 1: Japanese Patent No. 3809374

Non Patent Literature

Non Patent Literature 1: Yoshida, F., Uemori, T.: Int. J. Plasticity, 18, (2002), 661-686

SUMMARY

Technical Problem

However, the amount of plastic strain that occurs in the unloading process is very small, and due to the significantly small magnitude thereof, the amount of plastic strain that occurs during the unloading easily varies even if the same material is used to conduct tests to obtain the amount of the plastic strain. Accordingly, in the method described in Patent Literature 1, the coefficient of saturation speed of kinematic hardening of a yield surface cannot be accurately calculated, so that the stress-strain relation cannot be accurately calculated. Consequently, in the method described in Patent Literature 1, it is difficult to accurately predict the springback amount of an elastic-plastic material during press forming.

In the press-forming process, a material deforms when stress reversed from tension to compression or compression to tension is applied thereto. In view of this, it is very important to simulate the stress-strain relation when such reversed stress is applied to the material. However, the relation cannot be accurately simulated by the method disclosed in Patent Literature 1. The following describes this point.

FIG. 17 is a diagram illustrating a relation between stress and strain when stress is unloaded from a material after tensile deformation, and then tensile deformation (re-tensile deformation) is applied to the material again. In the unloading (compression) process, a non-linear curve is drawn as described above and non-linear behavior is observed in the same manner during the re-tension. Furthermore, the material deforms in the same manner as in the original tensile stress-strain relation when the tensile deformation proceeds. FIG. 18 is a diagram illustrating changes in gradient of stress with respect to strain (dσ/dε) when the unloading (compression) and the re-tensile deformation in FIG. 17 are applied. In FIG. 18, the horizontal axis represents stress (σ) and the vertical axis represents the gradient (dσ/dε). The gradient during the unloading (compression) and the gradient during the re-tension gradually decrease from high values in the initial stages of deformation because the material plastically deforms. The inventors of the present invention found in experiments that the gradient during the unloading and the gradient during the re-tension are symmetrical with respect to $\sigma_3$. In other words, the inventors found that the stress-strain relation resulted from the unloading (compression) and the re-tension exhibits point-symmetrical hysteresis.

However, when the stress-strain relation when the unloading (compression) and the re-tensile deformation are applied is calculated by the method described in Patent Literature 1, the gradient of stress with respect to strain is different between the unloading and the re-tension, so that the point-symmetrical hysteresis obtained in the experiments cannot be drawn. In other words, the stress-strain relation when the reversed stress is applied to the material cannot be accurately simulated by the method of Patent Literature 1.

The present invention has been made in view of the above-described problems, and an object thereof is to provide a stress-strain relation simulation method that enables the stress-strain relation of an elastic-plastic material to be accurately simulated. Another object of the present invention is to provide a springback prediction method that enables the springback amount of the elastic-plastic material during press forming to be accurately predicted. Still another object of the present invention is to provide a springback analyzer that can accurately analyze springback.

Solution to Problem

A stress-strain relation simulation method according to the present invention includes: an experimental-value acquisition step of plastically deforming an elastic-plastic material to acquire experimental values of a stress-strain relation; a first material-constant identification step of, by a computer, with a kinematic-hardening incremental vector $d\alpha_{ij}$ of a yield surface in an elastic-plastic constitutive model as Equation (1), the elastic-plastic constitutive model being defined as a function of stress and back stress, identifying material constants contained in the elastic-plastic constitutive model with the experimental values acquired at the experimental-value acquisition step; a second material-constant identification step of, by the computer, based on the Equation (1) into which the material constants identified at the first material-constant identification step are substituted and based on the experimental values acquired at the experimental-value acquisition step, identifying material constants contained in Equation (2); and a step of, by the computer, simulating the stress-strain relation of the elastic-plastic material with the Equation (1) and the Equation (2) into which the material constants identified are substituted, and the elastic-plastic constitutive model.

$$d\alpha_{ij} = \left[C\left(\frac{a}{Y}\right)(\sigma_{ij} - \alpha_{ij}) - C_0\rho X_{ij}\right]d\varepsilon^p_{eq} \quad (1)$$

$$C = C_0 + C_c \exp\left(-\frac{X^n_{eq}}{A}\right) \quad (2)$$

where
a: maximum value of movement of yield surface
Y: yield stress
$\alpha_{ij}$: movement vector of yield surface
$\sigma_{ij}$: stress vector
$X_{ij}$: yield—surface kinematic—hardening amount after stress reversal ($X_{eq}$ is equivalent value thereof)
$d\varepsilon^p_{eq}$: equivalent plastic—strain increment
$C_0$, $C_C$, A, n: material constants Moreover, in the stress-strain relation simulation method according to the present invention, variables $X_{ij}$, ρ, A, and n in the Equations (1) and (2) are represented by Equation (3).

$$\begin{aligned} &\text{If } \sigma_{eq} \geq \sigma_{eqmax}, \sigma_{eq} = \sigma_{eqmax} \\ &\quad X_{ij} = \alpha_{ij}, \rho = 1, A = A_1, n = n_1 \\ &\text{If } \sigma_{eq} < \sigma_{eqmax} \\ &\quad X_{ij} = \alpha^{tmp}_{ij} - \alpha_{ij}, \rho = \frac{1}{2}, A = A_2, n = n_2 \end{aligned} \quad (3)$$

where
$\sigma_{eq\ max}$: maximum value of equivalent stress when isotropic hardening is assumed
$\alpha^{tmp}_{ij}$: back stress at the time of stress reversal
$A_1$, $A_2$, $n_1$, $n_2$: material constants Moreover, in the stress-strain relation simulation method according to the present invention, as a method for applying plastic deformation to the elastic-plastic material at the experimental-value acquisition step, one method is used out of: a method in which stress is applied to the elastic-plastic material in a tensile direction to deform the elastic-plastic material plastically and is then unloaded; a method in which stress is applied to the elastic-plastic material in the tensile direction to deform the elastic-plastic material plastically and is then unloaded, and stress is applied in a compression direction to deform the elastic-plastic material plastically; and a method in which stress is applied to the elastic-plastic material in the tensile direction to deform the elastic-plastic material plastically and is then unloaded, and stress is applied again to the elastic-plastic material in the tensile direction to deform the elastic-plastic material plastically.

A springback-amount prediction method according to the present invention includes: an experimental-value acquisition step of plastically deforming an elastic-plastic material to acquire experimental values of a stress-strain relation; a first material-constant identification step of, by a computer, with a kinematic-hardening incremental vector $d\alpha_{ij}$ of a yield surface in an elastic-plastic constitutive model as Equation (1), the elastic-plastic constitutive model being defined as a function of stress and back stress, identifying material constants contained in the elastic-plastic constitutive model with the experimental values acquired at the experimental-value acquisition step; a second material-constant identification step of, by the computer, based on the Equation (1) into which the material constants identified at the first material-constant identification step are substituted and based on the experimental values acquired at the experimental-value acquisition step, identifying material constants contained in Equation (2); and a step of, by the computer, predicting a springback amount with the Equation (1) and the Equation (2) into which the material constants identified are substituted, and the elastic-plastic constitutive model.

$$d\alpha_{ij} = \left[C\left(\frac{a}{Y}\right)(\sigma_{ij} - \alpha_{ij}) - C_0 \rho X_{ij}\right] d\varepsilon_{eq}^p \quad (1)$$

$$C = C_0 + C_C \exp\left(-\frac{X_{eq}^n}{A}\right) \quad (2)$$

where
a: maximum value of movement of yield surface
Y: yield stress
$\alpha_{ij}$: movement vector of yield surface
$\sigma_{ij}$: stress vector
$X_{ij}$: yield—surface kinematic—hardening amount after stress reversal ($X_{eq}$ is equivalent value thereof)
$d\varepsilon^p_{eq}$: equivalent plastic—strain increment
$C_0$, $C_C$, A, n: material constants Moreover, in the springback-amount prediction method according to the present invention, variables $X_{ij}$, $\rho$, A, and n in the Equations (1) and (2) are represented by Equation (3).

$$\begin{aligned} &\text{If } \sigma_{eq} \geq \sigma_{eqmax}, \sigma_{eq} = \sigma_{eqmax} \\ &\quad X_{ij} = \alpha_{ij}, \rho = 1, A = A_1, n = n_1 \\ &\text{If } \sigma_{eq} < \sigma_{eqmax} \\ &\quad X_{ij} = \alpha_{ij}^{tmp} - \alpha_{ij}, \rho = \frac{1}{2}, A = A_2, n = n_2 \end{aligned} \quad (3)$$

where
$\sigma_{eq\ max}$: maximum value of equivalent stress when isotropic hardening is assumed
$\alpha^{tmp}_{ij}$: back stress at the time of stress reversal
$A_1$, $A_2$, $n_1$, $n_2$: material constants Moreover, in the springback-amount prediction method according to the present invention, as a method for applying plastic deformation to the elastic-plastic material at the experimental-value acquisition step, one method is used out of: a method in which stress is applied to the elastic-plastic material in a tensile direction to deform the elastic-plastic material plastically and is then unloaded; a method in which stress is applied to the elastic-plastic material in the tensile direction to deform the elastic-plastic material plastically and is then unloaded, and stress is applied in a compression direction to deform the elastic-plastic material plastically; and a method in which stress is applied to the elastic-plastic material in the tensile direction to deform the elastic-plastic material plastically and is then unloaded, and stress is applied again to the elastic-plastic material in the tensile direction to deform the elastic-plastic material plastically.

A springback analyzer according to the present invention predicts a springback amount of a press-formed product with a computer, and includes: a press-forming analysis unit that performs press-forming analysis to acquire shape, residual-stress distribution, and strain distribution of the press-formed product through analysis before die release; and a springback analysis unit that performs springback analysis based on the shape, the residual-stress distribution, and the strain distribution of the press-formed product to acquire the springback amount of the press-formed product after die release, wherein a kinematic-hardening incremental vector $d\alpha_{ij}$ of a yield surface in an elastic-plastic constitutive model that the press-forming analysis unit and the springback analysis unit have is represented by Equations (1) and (2).

$$d\alpha_{ij} = \left[C\left(\frac{a}{Y}\right)(\sigma_{ij} - \alpha_{ij}) - C_0 \rho X_{ij}\right] d\varepsilon_{eq}^p \quad (1)$$

$$C = C_0 + C_c \exp\left(-\frac{X_{eq}^n}{A}\right), \quad (2)$$

where
a: maximum value of movement of yield surface
Y: yield stress
$\alpha_{ij}$: movement vector of yield surface
$\sigma_{ij}$: stress vector
$X_{ij}$: yield—surface kinematic—hardening amount after stress reversal ($X_{eq}$ is equivalent value thereof)
$d\varepsilon^p_{eq}$: equivalent plastic—strain increment
$C_0$, $C_C$, A, n: material constants Moreover, in the springback analyzer according to the present invention, variables $X_{ij}$, $\rho$, A, and n in the Equations (1) and (2) are represented by Equation (3).

$$\begin{aligned} &\text{If } \sigma_{eq} \geq \sigma_{eqmax}, \sigma_{eq} = \sigma_{eqmax} \\ &\quad X_{ij} = \alpha_{ij}, \rho = 1, A = A_1, n = n_1 \\ &\text{If } \sigma_{eq} < \sigma_{eqmax} \\ &\quad X_{ij} = \alpha_{ij}^{tmp} - \alpha_{ij}, \rho = \frac{1}{2}, A = A_2, n = n_2 \end{aligned} \quad (3)$$

where
$\sigma_{eq\ max}$: maximum value of equivalent stress when isotropic hardening is assumed
$\alpha^{tmp}_{ij}$: back stress at the time of stress reversal
$A_1$, $A_2$, $n_1$, $n_2$: material constants Advantageous Effects of Invention By the stress-strain relation simulation method according to the present invention, the stress-strain relation of an elastic-plastic material can be accurately simulated. By the springback-amount prediction method according to the present invention, the springback amount of the elastic-plastic material can be accurately predicted. By the springback analyzer according to the present invention, the springback amount of a press-formed product can be accurately predicted.

DESCRIPTION OF EMBODIMENTS

Principle of Present Invention

The inventors of the present invention focused on the Yoshida-Uemori model that was considered to be accurate among elastic-plastic constitutive models defined as functions of stress and back stress disclosed, clarified problematic points that the Yoshida-Uemori model had, and constructed a new elastic-plastic constitutive model. A principle of the present invention will be described first.

Figure 1A:
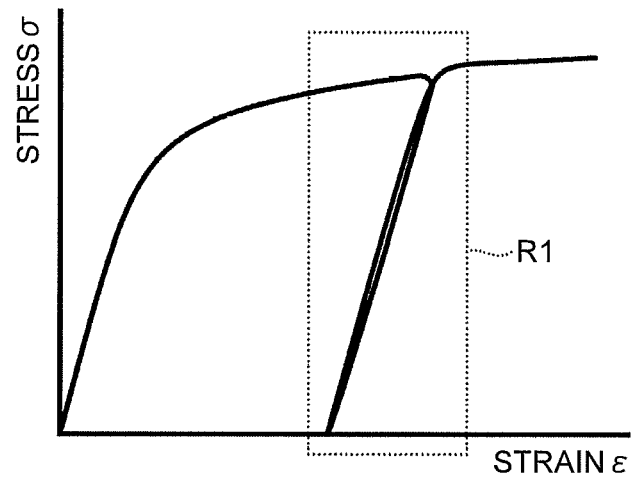
FIG. 1A is an explanatory diagram for explaining a principle of the present invention.
Figure 1B:
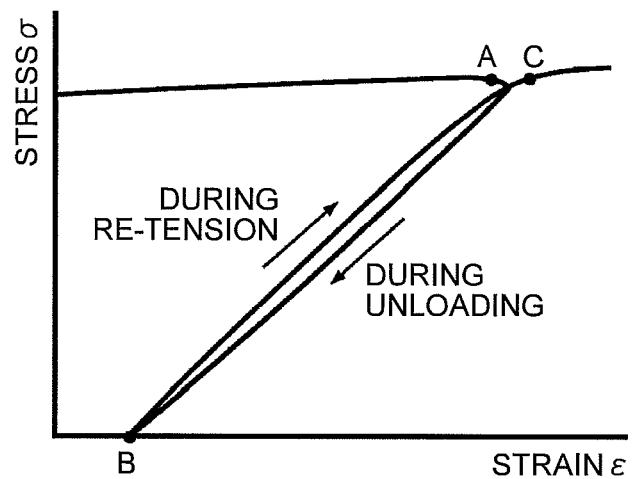
FIG. 1B is an explanatory diagram for explaining the principle of the present invention.

FIG. 1A is a diagram illustrating one example of a stress-strain relation when tensile deformation is applied to a material and is unloaded, and then re-tensile deformation is applied thereto. FIG. 1B is an enlarged view of the region R1 indicated in FIG. 1A. As depicted in FIG. 1B, the stress-strain relation exhibits hysteresis including non-linear curves during unloading (from the point A to the point B) and during re-tension (from the point B to the point C). In this manner, even for the cases of tension, unloading, and re-tension without compression, the stress-strain relation exhibits non-linear curves during the unloading and during the re-tension.

However, this region is handled as an elastic-deformation region in the elastic-plastic constitutive model of the Yoshida-Uemori model, where the stress-strain relation is assumed to be linear. This results in the problem that the hysteresis of the stress-strain relation cannot be accurately reproduced even for deformation without compression as depicted in FIG. 1A and FIG. 1B, and difference between the behavior during deformation with compression and the actual behavior becomes larger.

In the elastic-plastic constitutive model of Yoshida-Uemori model, the radius of the yield surface (elastic-deformation region) is generally large. However, as described above, actually when tensile deformation is applied and unloaded, and then re-tensile deformation is applied thereto, the elastic deformation region is small and the radius of the yield surface is small. In view of this, the inventors first considered making a smaller radius of the yield surface in order to make a smaller elastic-deformation region where the gradient of stress with respect to strain in regions of unloading and re-tension is constant so as to make the most part of the region as a work-hardening (plastic deformation) region.

Figure 2:
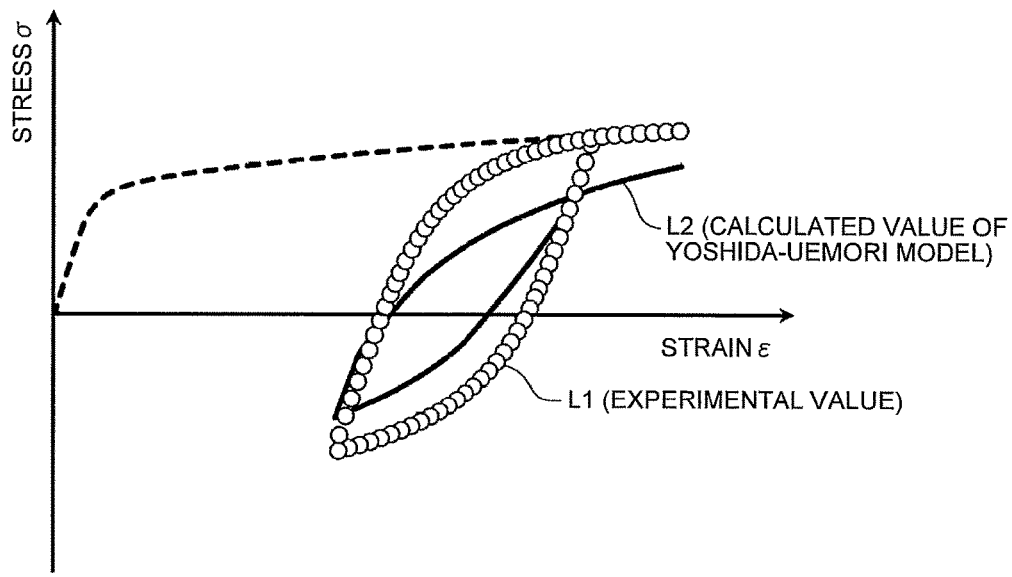
FIG. 2 is an explanatory diagram for explaining the principle of the present invention.

FIG. 2 illustrates a stress-strain relation when tensile-deformation is applied to a material, and after unloading and compression (hereinafter, referred to as "unloading-compression"), re-tensile deformation is applied thereto. In FIG. 2, the curve L1 represents experimental values and the curve L2 represents calculated values of the Yoshida-Uemori model when the radius of the yield surface is set to be small. As can be seen in FIG. 2, the experimental values and the calculated values are significantly different. The inventors studied on how these values differ and focused on two viewpoints. The first viewpoint is that the stress-strain gradient is substantially the same between the unloading-compression and the re-tension in the experimental values, whereas the stress-strain gradient is different between the unloading-compression and the re-tension in the calculated values. The second viewpoint is that the stress of a calculated value is smaller than the stress of an experimental value at a certain strain amount in both of the unloading-compression and the re-tension. The following describes these first and second viewpoints.

<First Viewpoint>

Figure 3:
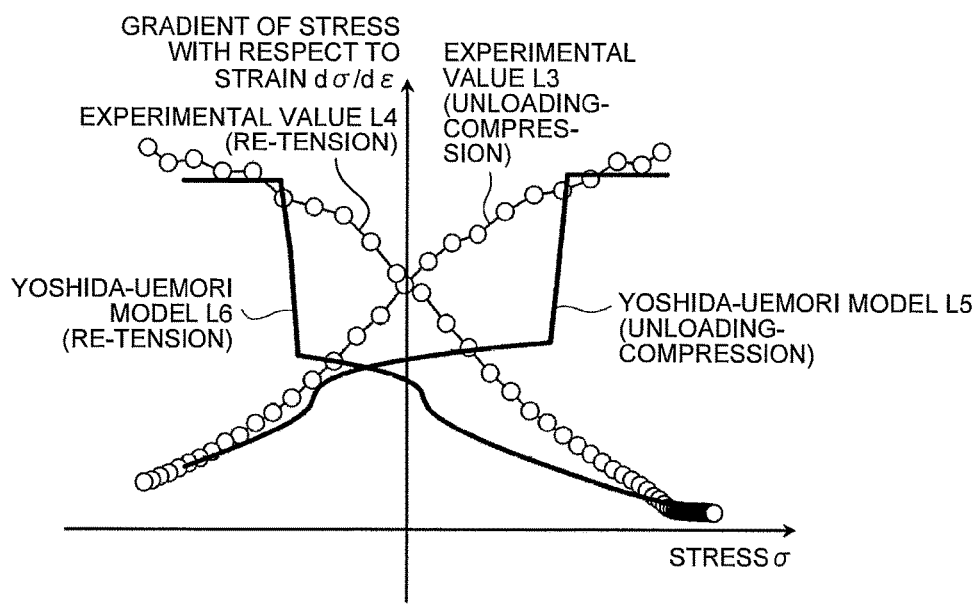
FIG. 3 is an explanatory diagram for explaining the principle of the present invention.

To study the first viewpoint, changes in the gradient of stress with respect to strain ($d\sigma/d\varepsilon$) when unloading-compression is applied and then the re-tension is applied (i.e., gradients of segments in FIG. 2) were checked. Specifically, as depicted in FIG. 3, check results were compiled into a graph in which the horizontal axis represents stress ($\sigma$) and the vertical axis represents the gradient ($d\sigma/d\varepsilon$) of stress with respect to strain. In FIG. 3, the curve L3 represents changes in stress-strain gradient during the unloading-compression process in the experimental values, and the curve L4 represents changes in stress-strain gradient during the re-tension process in the experimental values. The curve L5 represents changes in stress-strain gradient during the unloading-compression process in the calculated values of the Yoshida-Uemori model, and the curve L6 represents changes in stress-strain gradient during the re-tension process in the calculated values of the Yoshida-Uemori model. It can be seen from FIG. 3 that the curve L3 representing changes in stress-strain gradient during the unloading-compression in the experiment and the curve L4 representing changes in stress-strain gradient during the re-tension in the experiment are axially symmetrical with respect to the vertical axis passing through the intersection of the curve L3 and the curve L4. In contrast, it can be seen that the curve L5 representing changes in stress-strain gradient during the unloading-compression in the calculated values and curve L6 representing changes in stress-strain gradient during the re-tension in the calculated values clearly exhibit axially asymmetry proportions with respect to the vertical axis passing through the intersection of the curve L5 and the curve L6.

Figure 4:
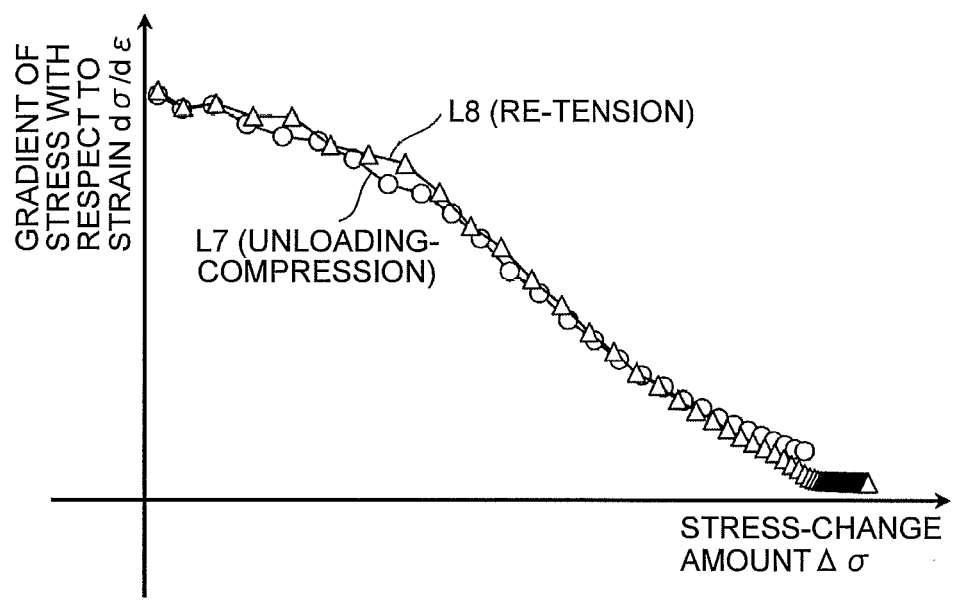
FIG. 4 is an explanatory diagram for explaining the principle of the present invention.
Figure 17:
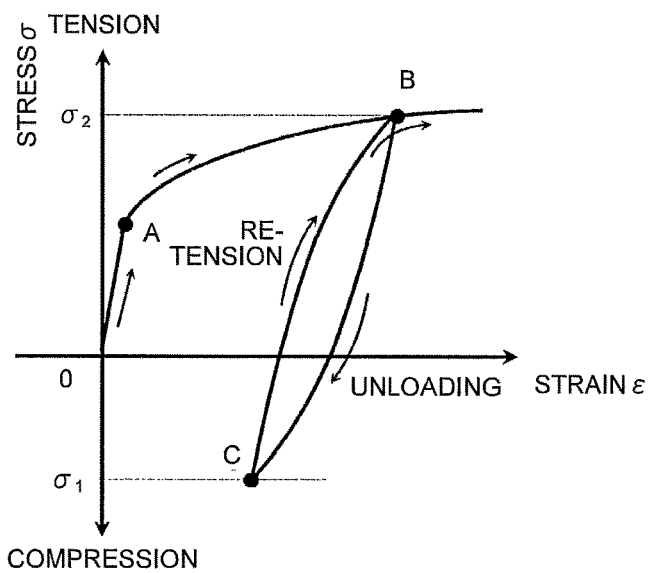
FIG. 17 is an explanatory diagram for explaining problems to be solved by the present invention.
Figure 18:
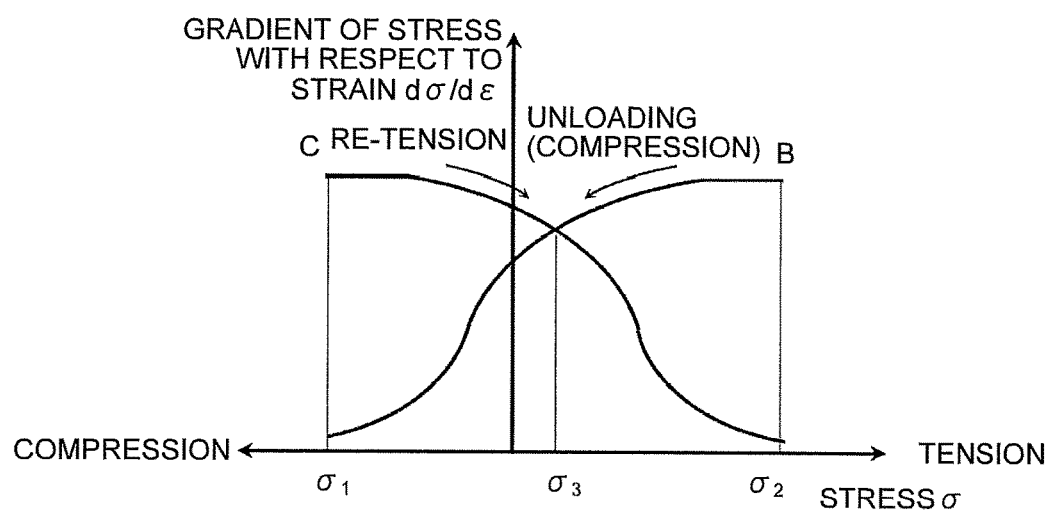
FIG. 18 is an explanatory diagram for explaining the problems to be solved by the present invention.

In view of this, to clarify the characteristics of the stress-strain gradient in the unloading-compression and the re-tension, the inventors thought of organizing the relation between a stress-change amount after the stress reversal and the stress-strain gradient (dσ/dε) in terms of the unloading-compression and the re-tension. The stress-change amount after the stress reversal is a stress-change amount Δσ that indicates how much stress has changed after the stress reversal (unloading from the point B or re-tension from the point C in FIG. 17). FIG. 4 is a diagram, in which the vertical axis represents the gradient (dσ/dε) and the horizontal axis represents the stress-change amount Δσ, indicating relations between the gradient and the stress-change amount in the unloading-compression process and in the re-tension process. In FIG. 4, the curve L7 represents the relation in the unloading-compression process, and the curve L8 represents the relation in the re-tension process. As seen in FIG. 4, the stress-strain gradient is substantially the same between the unloading-compression process (curve L7) and the re-tension process (curve L8). The inventors found from this that the gradient of the stress-strain relation, i.e., hardening behavior (behavior during work hardening) of the material, is determined by how much the stress has changed after the stress reversal regardless of either compression or re-tension.

The inventors studied on the problematic points of the Yoshida-Uemori model on the assumption of the above-described findings. The inventors focused on the movement of the yield surface (back stress) in the elastic-plastic constitutive model. The movement of the yield surface is directly attributed to work hardening of the material. Accordingly, by changing the extent of the movement, the stress-strain relation can be changed. Equation (4) described below represents an incremental equation of a movement vector $\alpha^*_{ij}$ of the yield surface of the Yoshida-Uemori model.

$$d\alpha^*_{ij} = \left[ C\left(\frac{a}{Y}\right)(\sigma_{ij} - \alpha_{ij}) - \sqrt{\frac{a}{a^*_{eq}}} \alpha^*_{ij} \right] d\varepsilon^p_{eq} \quad (i, j = x, y, z) \quad (4)$$

The coefficient C in Equation (4) is a material constant that controls the saturation speed of kinematic hardening of the yield surface, a is a radius difference between a bounding surface and the yield surface, Y is yield stress, $\alpha^*_{eq}$ is an equivalent value of $\alpha^*_{ij}$, and $d\varepsilon^p_{eq}$ is an equivalent plastic-strain increment.

Based on the finding that the hardening behavior of the material is determined by how much the stress has changed after the stress reversal regardless of either compression or re-tension, the inventors thought of modifying the decrement term in the incremental equation of $\alpha^*_{ij}$. Because $\alpha^*_{ij}$ included in the decrement term defines the change amount from the origin, a difference due to this decrement term appears in hardening behavior between compression and re-tension.

In view of this, the inventors thought of expressing the decrement term in the incremental equation of the movement vector $\alpha^*_{ij}$ of the yield surface in the elastic-plastic constitutive model, using a vector $X_{ij}$ representing the amount of kinematic hardening of the yield surface after the stress reversal as given in Equation (5).

$$d\alpha^*_{ij} = \left[ C\left(\frac{a}{Y}\right)(\sigma_{ij} - \alpha_{ij}) - \rho X_{ij} \right] d\varepsilon^p_{eq} \quad (5)$$

Furthermore, the inventors thought of switching between ρ and $X_{ij}$ in Equation (5) in accordance with the stress applied to the material. The following describes this switching method. In the deformation process, the variables in Equation (5) were considered separately depending on cases as given in Equations (6) below, in one case that an equivalent value (converted value into a uniaxial tensile stress) $\sigma_{eq}$ of the current stress that is three-dimensionally applied to the material is maximum, i.e., the case that the current stress is larger than the previous maximum value a $\sigma_{eqmax}$ (maximum value of equivalent stress when isotropic hardening is assumed), and in the other case.

$$\left. \begin{array}{l} \text{If } \sigma_{eq} \geq \sigma_{eqmax}, \sigma_{eq} = \sigma_{eqmax} \\ \quad X_{ij} = \alpha^*_{ij}, \rho = 1 \\ \text{If } \sigma_{eq} < \sigma_{eqmax} \\ \quad X_{ij} = \alpha^{*tmp}_{ij} - \alpha_{ij}, \rho = \frac{1}{2} \end{array} \right\} \quad (6)$$

$\alpha^{*tmp}_{ij}$ herein is back stress (yield surface vector) at the time of stress reversal, and is a value that does not change until the next stress reversal occurs. These equations can express the characteristic of the stress-strain relation determining the hardening behavior of the material with the amount of kinematic hardening after the stress reversal.

The expression "If $\sigma_{eq} \geq \sigma_{eqmax}$, $\sigma_{eq} = \sigma_{eqmax}$" in Equation (6) means that the currently applied stress is the maximum value in the past because this is the case that the currently applied stress is higher than the stresses having been applied so far. The above-described case is the case that, for example, after the unloading-compression, re-tension is applied to the material, the stress returns to a value at the unloading, and then tension is applied. This case corresponds to the case at and after the point C in FIG. 1B (the stress is the same between the point A and the point C).

The expression "If $\sigma_{eq} < \sigma_{eqmax}$" in Equation (6) means when the currently applied stress is lower than the stresses having been applied so far, which is thus a state of from unloading-compression to re-tension applied to the material, for example. This case corresponds to the case of proceeding from the point A to the point B, and then proceeding from the point B to the point C in FIG. 1B. In this case, $\sigma_{eqmax}$ is the stress at the point A.

As described above, by using Equation (5) and Equation (6), the hardening behavior of the material can be formulated with the change amount of stress after the stress reversal.

<Second Viewpoint>

Next, the inventors focused on the coefficient C in FIG. 4 to solve the problem that "the stress of a calculated value is smaller than the stress of an experimental value at a certain strain amount in both of the unloading-compression and the re-tension" of the above-described second viewpoint. The coefficient C is a material constant that controls the saturation speed of kinematic hardening of the yield surface. The stress-strain gradient after the stress reversal is higher as the saturation speed of kinematic hardening of the yield surface is higher. As seen in FIG. 2, the gradient of the curve L2 of the calculated values is smaller than the gradient of the curve L1 of the experimental values, and thus it can be considered that the stress in the calculated values is lower than the stress in the experimental values. Accordingly, it can be considered that the saturation speed of kinematic hardening of the yield surface should be increased, i.e., the work-hardening ratio should be increased to reduce errors of the curve L2 of the calculated values. However, even if the coefficient C is simply increased to increase the saturation speed of kinematic hardening of the yield surface, the calculated values do not sufficiently match the experimental values.

In view of this, the inventors thought of calculating ideal values for the coefficient C to match the calculated values of the stress-strain relation with the experimental values thereof in the unloading-compression process and in the re-tension process, and studying based on these ideal values. To begin with, Equation (5) is modified into Equation (7) below.

$$d\alpha_{ij}^* = \left[C\left(\frac{a}{Y}\right)(\sigma_{ij} - \alpha_{ij}) - C\rho X_{ij}\right]d\varepsilon_{eq}^p \quad (7)$$

When terms within the brackets in Equation (5) are focused, to increase the saturation speed of kinematic hardening of the yield surface, the incremental term may be increased. Accordingly, the inventors thought of Equation (8) in which the decrement term is fixed with $C_0$ that is a constant the same as the coefficient identified in the Yoshida-Uemori model.

$$d\alpha_{ij}^* = \left[C\left(\frac{a}{Y}\right)(\sigma_{ij} - \alpha_{ij}) - C_0\rho X_{ij}\right]d\varepsilon_{eq}^p \quad (8)$$

Figure 5:
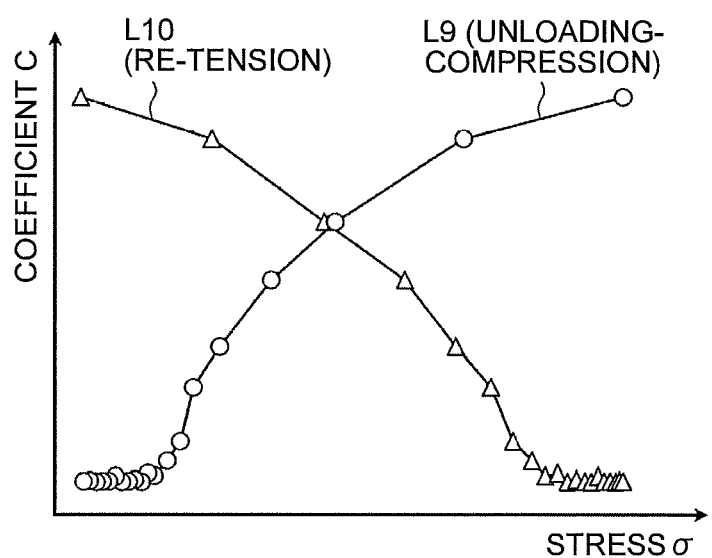
FIG. 5 is an explanatory diagram for explaining the principle of the present invention.

The ideal values were calculated, with the experimental values and Equation (8), by finding a coefficient C for matching the stress-strain relation calculated by Equation (8) with the experimental values. FIG. 5 represents the ideal values of the calculated coefficient C along the vertical axis and the stress σ along the horizontal axis. In FIG. 5, the curve L9 represents the ideal values of the coefficient C in the unloading-compression process, and the curve L10 represents the ideal values of the coefficient C in the re-tension process.

Figure 6:
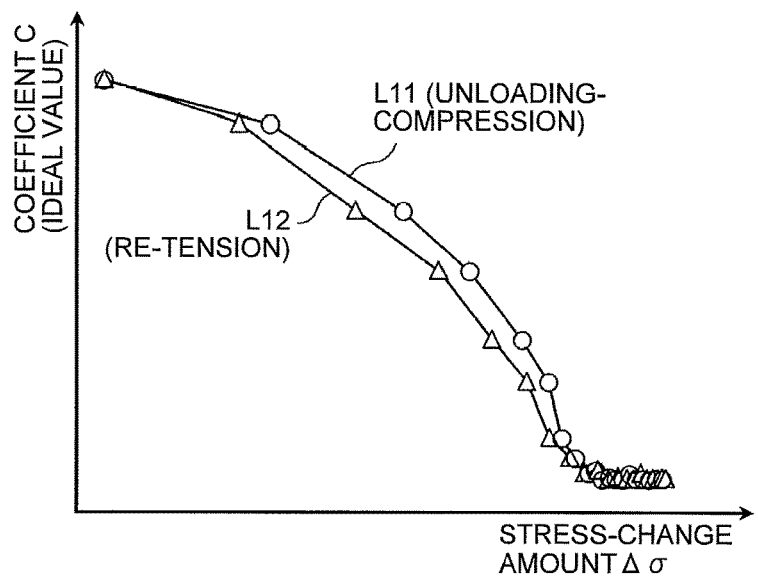
FIG. 6 is an explanatory diagram for explaining the principle of the present invention.

To clarify the characteristics of the ideal values of the coefficient C, the inventors organized the relation between the stress-change amount after the stress reversal, i.e., the stress-change amount Δσ that indicates how much stress has changed after the stress reversal, and the ideal values of the coefficient C in the unloading-compression process and in the re-tension process. FIG. 6 is a diagram, in which the vertical axis represents the ideal values of the coefficient C and the horizontal axis represents the stress-change amount Δσ, indicating the relation between the ideal values of the coefficient C and the stress-change amount Δσ in the unloading-compression process and in the re-tension process. In FIG. 6, the curve L11 represents the relation in the unloading-compression process, and the curve L12 represents the relation in the re-tension process.

As seen in FIG. 6, the curve L11 for the unloading-compression process is substantially the same as the curve L12 for the re-tension process. In FIG. 6, the coefficient C marks high values in the initial stages of the unloading-compression process and the re-tension process, and exhibits behavior asymptotic to lower values as the stress-change amount from the stress reversal increases. Thus, it is considered that the coefficient C can be approximated on a graph of an exponential function. The inventors then decided to describe the coefficient C as a function of the stress-change amount as given in Equation (2) below.

$$C = C_0 + C_c \exp\left(-\frac{X_{eq}^n}{A}\right) \quad (2)$$

where

If $\sigma_{eq} \geq \sigma_{eq\,max}$, $\sigma_{eq} = \sigma_{eq\,max}$ $X_{ij} = \alpha_{ij}^*$, $A = A_1$, $n = n_1$ If $\sigma_{eq} < \sigma_{eq\,max}$ $X_{ij} = \alpha_{ij}^{*tmp} - \alpha_{ij}^*$, $A = A_2$, $n = n_2$ $X_{eq}$ herein is an equivalent value of $X_{ij}$, and $C_0$, $C_C$, $A_1$, $A_2$, $n_1$, and $n_2$ are material constants. The coefficient $C_0$ is a material constant for a convergence value of the coefficient C, and the material constant C identified in the Yoshida-Uemori model is substituted therefor. The coefficient $C_C$ is a material constant for the increased amount of the coefficient C, and the coefficients $A_1$, $A_2$, $n_1$, and $n_2$ are material constants for saturation speed (work-hardening rate) of the coefficient C.

To define the coefficient C for indicating the saturation speed of kinematic hardening of the yield surface, a function of strain is used in Patent Literature 1 as described above, and thus the range of changes is small and variations are too large to determine the coefficient C by experiments. In contrast, because the present invention assumes that the coefficient C is determined by a function of stress, the range of changes is large and variations are small, and thus accurate results can be obtained.

As described above, in the present invention, the stress-strain relation in the unloading-compression process and in the re-tension process is determined based on the stress-change amount after the stress reversal, whereby the stress-strain relation can be expressed without difference from the relation indicated by the experimental values in the unloading-compression process and in the re-tension process. In other words, by the present invention, the calculated values of the stress-strain relation in the unloading-compression process and in the re-tension process (and the compression process) can be matched with the experimental values thereof, and consequently, the springback amount can be accurately predicted.

In the foregoing description, explanation has been given with the Yoshida-Uemori model as an example for the elastic-plastic constitutive model defined as a function of stress and back stress. Accordingly, as an expression for a kinematic-hardening incremental vector $d\alpha_{ij}$, the expression $d\alpha_{ij}^*$ used in the Yoshida-Uemori model (expression using "*") has been used. However, the present invention does not use the Yoshida-Uemori model as a precondition, and the kinematic-hardening incremental vector $d\alpha_{ij}$ of the present invention can be used as a kinematic-hardening incremental vector of the yield surface in elastic-plastic constitutive models conventionally proposed. Furthermore, the elastic-plastic constitutive model can be constituted by the kinematic-hardening incremental vector $d\alpha_{ij}$ alone. In the Yoshida-Uemori model (see Equation (4)), a denotes the radius difference between the bounding surface and the yield surface. By contrast, in the present invention in which the kinematic-hardening incremental vector (see Equation (8)) is generalized as in Equation (1) below, a is the maximum value of the kinematic-hardening amount of the yield surface.

$$d\alpha_{ij} = \left[C\left(\frac{a}{Y}\right)(\sigma_{ij} - \alpha_{ij}) - C_0\rho X_{ij}\right]d\varepsilon_{eq}^p \quad (1)$$

First Embodiment

Stress-Strain Relation Simulation Method

Figure 7:
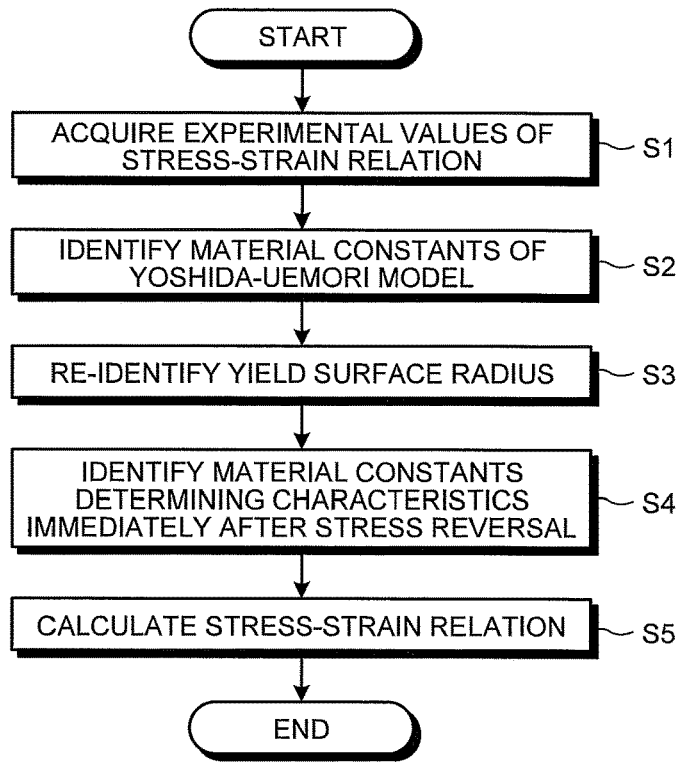
FIG. 7 is a flowchart illustrating a flow of a stress-strain relation simulation method according to a first embodiment of the present invention.

A stress-strain simulation method as one embodiment of the present invention will be described hereinafter with reference to FIG. 7. FIG. 7 is a flowchart illustrating a flow of the stress-strain relation simulation method of this first embodiment. In the processing at step S1, an operator acquires experimental values of the stress-strain relation of an elastic-plastic material. To acquire the experimental values, the operator conducts a tension→unloading→compression test in which stress is applied to the elastic-plastic material in the tensile direction to deform the elastic-plastic material plastically and is then unloaded, and stress is applied in the compression direction to deform the elastic-plastic material plastically. The operator also conducts a tension→unloading→re-tension test in which stress is applied in the tensile direction to deform the elastic-plastic material plastically and is then unloaded, and stress is applied again in the tensile direction to deform the elastic-plastic material plastically.

In the present embodiment, experimental values are acquired by conducting the tension→unloading→compression test and the tension→unloading→re-tension test, but alternatively, only either one of these two tests may be conducted. Instead of these two tests, a tension→unloading test in which stress is applied in the tensile direction to deform the elastic-plastic material plastically and is then unloaded may be conducted.

In the processing at step S2, a computer such as a personal computer (PC) identifies other material constants Y, B, C, b, m, $R_{sat}$, and h described in Non Patent Literature 1 included in the Yoshida-Uemori model with the experimental values of the stress-strain relation acquired in the processing at step S1.

In the processing at step S3, the computer uses the experimental values of the stress-strain relation acquired in the processing at step S1 to re-identify the stress (yield surface radius) when the tangential gradient $d\sigma/d\varepsilon$ of stress versus strain starts to decrease as a material constant Y (yield stress).

In the processing at step S4, the computer identifies the material constants $C_C$, $A_1$, $A_2$, $n_1$, and $n_2$ that determine characteristics immediately after the stress reversal with Equation (1) that is an elastic-plastic constitutive model of the present invention using the material constants identified in the processing at step S2 and step S3. As the coefficient $C_0$ in Equation (1), the coefficient C in the Yoshida-Uemori model identified at step S2 is used.

In the processing at step S5, when the material constants identified in the processing from step S2 to S4 are substituted into the elastic-plastic constitutive models (1) and (2), the computer calculates the stress-strain relation of the elastic-plastic material with the elastic-plastic constitutive models into which the constants are substituted. Through these steps S1 to S5, a series of stress-strain relation simulation processing is completed.

Second Embodiment

Springback-Amount Prediction Method

Figure 8:
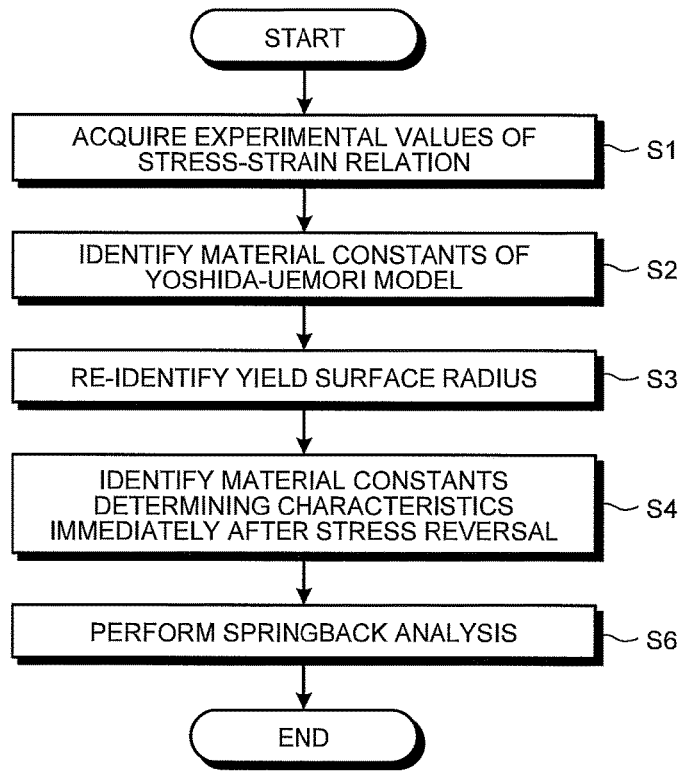
FIG. 8 is a flowchart illustrating a flow of a springback-amount prediction method according to a second embodiment of the present invention.

A springback amount prediction method as one embodiment of the present invention will be described hereinafter with reference to FIG. 8. FIG. 8 is a flowchart illustrating a flow of the springback amount prediction method of this embodiment. Because the processing at step S1 to step S4 are the same as those in FIG. 7, the description thereof will be omitted. In the processing at step S6, when the material constants identified in the processing at step S2 to step S4 are substituted into the elastic-plastic constitutive models (1) and (2), the computer predicts the springback amount by performing springback analysis using the elastic-plastic constitutive models into which the material constants are substituted.

Third Embodiment

The elastic-plastic constitutive models containing the kinematic-hardening incremental vector $d\alpha_{ij}$ formulated in the first embodiment is incorporated into finite-element-method analysis software, whereby a springback analyzer is configured. The configuration of this springback analyzer 1 will be described hereinafter with reference to a block diagram illustrated in FIG. 9.

[Springback Analyzer]

Figure 9:
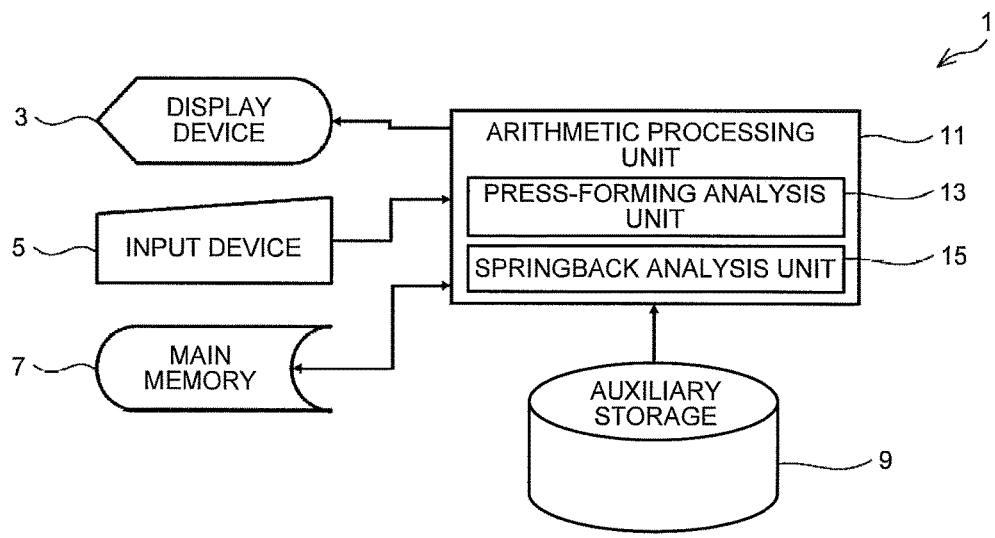
FIG. 9 is a block diagram illustrating a configuration of a springback analyzer according to a third embodiment of the present invention.

The springback analyzer 1 is configured with a personal computer (PC), for example, and includes a display device 3, an input device 5, a main memory 7, an auxiliary storage 9, and an arithmetic processing unit 11 as depicted in FIG. 9. The display device 3, the input device 5, the main memory 7, and the auxiliary storage 9 are connected to the arithmetic processing unit 11, and each function is performed in accordance with an instruction from the arithmetic processing unit 11. The display device 3 is configured with a liquid crystal monitor and other components and is used to display calculation results, for example. The input device 5 is configured with a keyboard and a mouse, for example, and is used for input from an operator, for example.

The main memory 7 is configured with a RAM and other components and is used to temporarily store therein data used in the arithmetic processing unit 11 or to perform computation, for example. The auxiliary storage 9 is configured with a hard disk and other components and is used to store therein data, for example. The arithmetic processing unit 11 is configured with a central processing unit (CPU) and other components of a PC, for example. The arithmetic processing unit 11 includes a press-forming analysis unit 13 and a springback analysis unit 15. These units (13, 15) are implemented when the CPU, for example, of the arithmetic processing unit 11 executes a predetermined program. The following describes these units (13, 15) in detail.

<Press-Forming Analysis Unit>

The press-forming analysis unit 13 performs press-forming analysis on a press-formed product to acquire shape information, stress distribution, and strain distribution after press forming (before die release). Into the press-forming analysis unit 13, an elastic-plastic constitutive model defined as a function of stress and back stress is input, and the kinematic-hardening incremental vector $d\alpha_{ij}$ thereof is that given in Equation (1) above.

<Springback Analysis Unit>

The springback analysis unit 15 performs springback analysis based on the shape information, the stress distribution, and the strain distribution before die release obtained by the press-forming analysis unit 13 and given physical properties to acquire the springback amount after die release. The elastic-plastic constitutive model defined as a function of stress and back stress is input into the springback analysis unit 15 in the same manner as the press-forming analysis unit 13, and the kinematic-hardening incremental vector $d\alpha_{ij}$ thereof is the same as that of Equation (1) above.

Material constants in the elastic-plastic constitutive model that the press-forming analysis unit 13 and the springback analysis unit 15 have are identified by performing the processing at step S1 to step S4 depicted in FIG. 7. Thus, when the springback analyzer 1 of the present embodiment performs springback analysis, the processing at step S1 to step S4 may be performed on the material used in press forming to identify the material constants of Equations (1) and (2), and the material constants may be substituted into the elastic-plastic constitutive model that the press-forming analysis unit 13 and the springback analysis unit 15 have.

Using the springback analyzer 1 as described above can accurately reproduce the stress-strain relation in unloading-compression and re-tension applied to the material in the press-forming process, whereby the springback amount can be accurately predicted.

Figure 10:
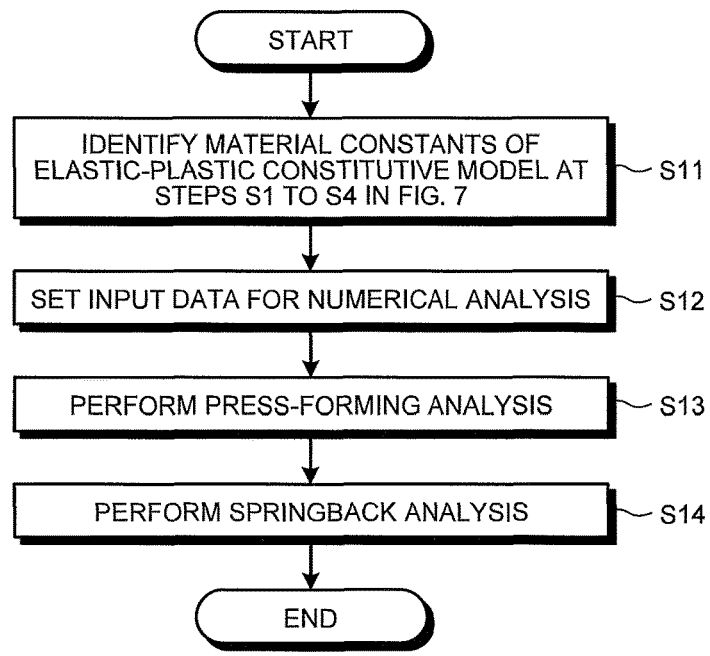
FIG. 10 is a flowchart illustrating a flow of a springback-analysis method using the springback analyzer according to the third embodiment of the present invention.

A method for performing springback analysis using the above-described springback analyzer 1 will be described hereinafter with reference to FIG. 10. The arithmetic processing unit 11 performs the above-described processing at step S1 to step S4 to identify the material constants contained in the elastic-plastic constitutive models (1) and (2) (step S11).

In the processing at step S12, the arithmetic processing unit 11 prepares, in addition to the material constants identified in the processing at step S11, pieces of data required for press-forming analysis, such as data on a die, data on a blank, and data such as forming speed, and sets these pieces of data as input data.

In the processing at step S13, upon receiving the input data thus set in the processing at step S12, the press-forming analysis unit 13 installed in the springback analyzer 1 performs press-forming analysis.

In the processing at step S14, the springback analysis unit 15 performs springback analysis based on results of the press-forming analysis at step S13 to predict the springback amount of the elastic-plastic material during the press forming. Through these steps S11 to S14, a series of springback amount prediction processing is completed.

Example 1

In Example 1, each of (1) tension→unloading test, (2) tension→unloading→compression test, and (3) tension-→unloading→re-tension test was conducted on a steel sheet JSC980Y having a sheet thickness of 1.2 millimeters, experimental values of the stress-strain relation of the steel sheet JSC980Y were acquired in each test. The material constants of the elastic-plastic constitutive model were identified with the experimental values acquired in each test, and the stress-strain relation of the steel sheet JSC980Y was calculated with the elastic-plastic constitutive model the material constants of which were identified.

Figure 11:
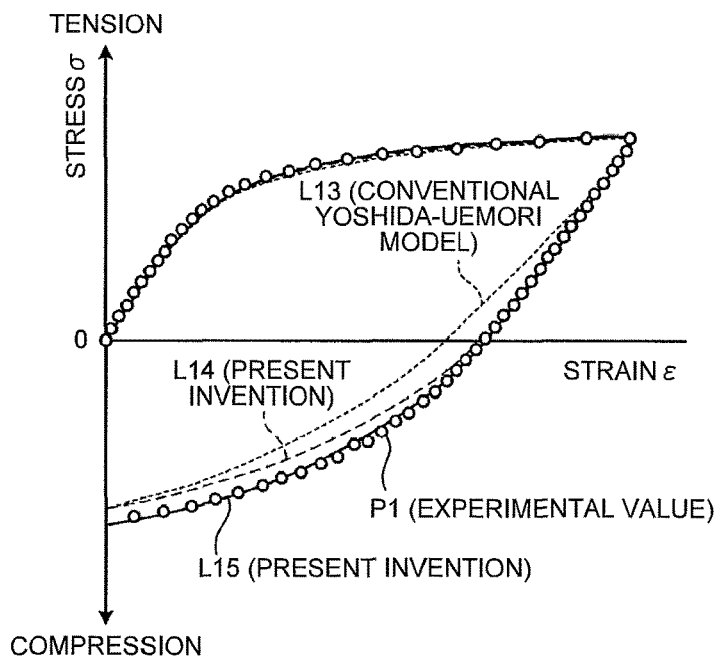
FIG. 11 is an explanatory diagram illustrating experimental results in Example 1 of the present invention.

FIG. 11 is a diagram illustrating each stress-strain relation. The curve L13 represents the stress-strain relation calculated with the conventional Yoshida-Uemori model. The curve L14 represents the stress-strain relation of the present invention calculated based on the experimental values P1 of the stress-strain relation obtained from the tension→unloading test. The curve L15 represents the stress-strain relation of the present invention calculated based on the experimental values P1 of the stress-strain relation obtained from the tension→unloading→compression test. It is apparent from FIG. 11 that the curves L14 and L15 of the stress-strain relation calculated based on the experimental values P1 match the experimental values P1 at a higher accuracy than the curve L13 representing the stress-strain relation calculated with the Yoshida-Uemori model.

As described above, in the present embodiment, experimental values of a stress-strain relation obtained from any one test out of (1) tension→unloading test, (2) tension→unloading→compression test, and (3) tension→unloading→re-tension test are used to identify the material constants of the elastic-plastic constitutive model of the present invention. The material constants identified are then used to calculate the coefficient C that controls the saturation speed of kinematic hardening of the yield surface represented by Formula (2). Furthermore, the material constants and the coefficient C calculated are substituted into the elastic-plastic constitutive model. It was confirmed in the present example that the stress-strain relation was able to be accurately calculated in a manner described above.

Example 2

Figure 12A:
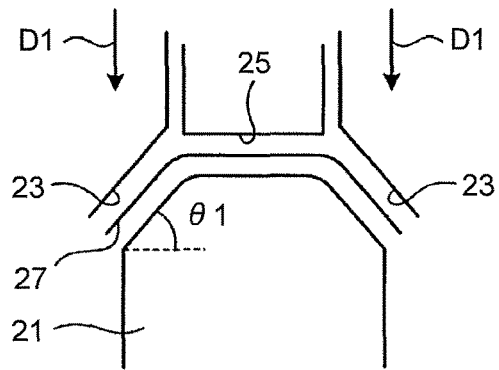
FIG. 12A is an explanatory diagram for explaining an experimental procedure in Example 2 of the present invention.
Figure 12B:
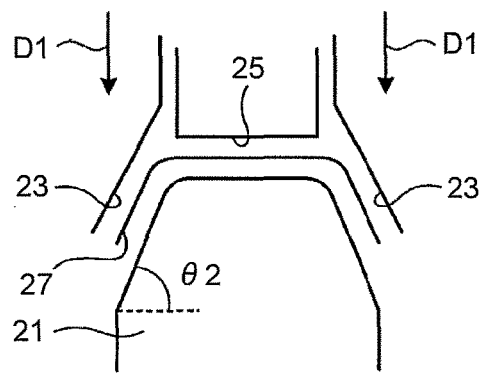
FIG. 12B is an explanatory diagram for explaining the experimental procedure in Example 2 of the present invention.

In Example 2, to verify the usefulness of the present invention for springback-amount prediction in press-forming analysis, a simple bending test was conducted on a steel sheet JSC980Y having a sheet thickness of 1.2 millimeters. FIGS. 12A and 12B are schematic diagrams for explaining an experimental procedure of the simple bending test. In this simple bending test, to begin with, as depicted in FIG. 12A, this steel sheet 27 was arranged between a punch 21, dies 23, and a pad 25. The steel sheet was subjected to simple bending forming (first bending) at a bending angle θ1 (=30° to 75°) by moving the dies 23 and the pad 25 in the arrow D1 directions. Subsequently, as depicted in FIG. 12B, the steel sheet 27 was subjected to simple bending forming (second bending) again at a bending angle θ2 (=45° to 75°) larger than the bending angle θ1. In this manner, loading→unloading→re-loading→re-unloading deformation was applied to bent portions of the steel sheet 27.

Figure 13:
FIG. 13 is an explanatory diagram for explaining a springback-evaluation method for experimental results in Example 2 of the present invention.
Figure 14:
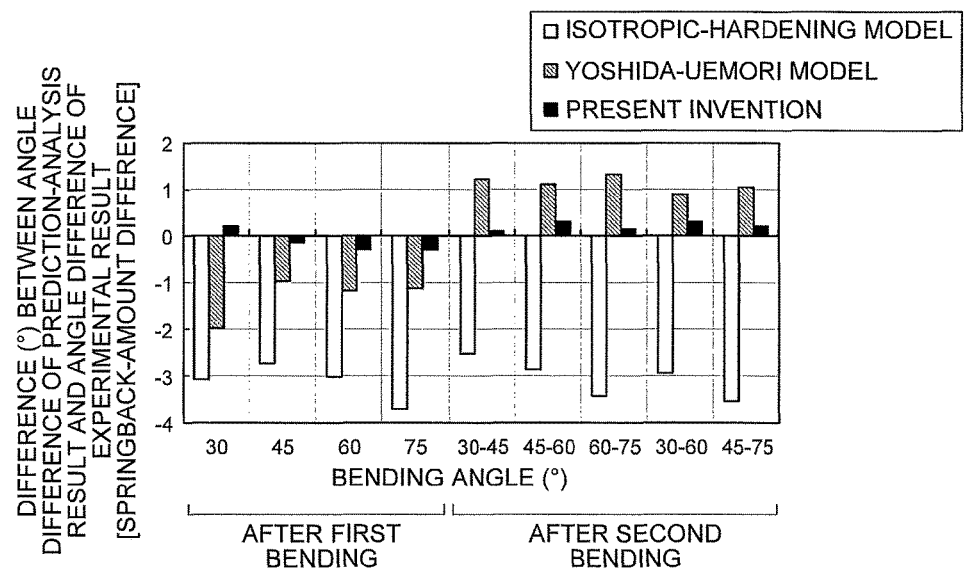
FIG. 14 is an explanatory diagram illustrating the experimental results in Example 2 of the present invention.

The bending angle φ of the steel sheet 27 after springback was defined as depicted in FIG. 13. FIG. 14 illustrates differences (springback-amount differences) between angle differences of prediction-analysis results (springback amounts of prediction-analysis results) and angle differences of experimental results (springback amounts of experimental results) with respect to bending angles φ after the first bending and the second bending. As depicted in FIG. 14, it was confirmed that the angle differences predicted by the present invention are less different from the angle differences of the experimental values than the angle differences predicted by the conventional isotropic-hardening model and the angle differences predicted by the Yoshida-Uemori model, in both of the first bending and the second bending. The above matters have demonstrated that the present invention can accurately predict the springback amount.

As described above, in the stress-strain relation simulation method of the present invention, experimental values of a stress-strain relation of an elastic-plastic material are used to calculate material constants contained in an elastic-plastic constitutive model. The material constants calculated are then used to calculate a coefficient C that controls the saturation speed of kinematic hardening of a yield surface represented by Equation (2). Furthermore, the material constants and the coefficient C calculated are substituted into the elastic-plastic constitutive model to calculate the stress-strain relation of the elastic-plastic material. With this stress-strain relation simulation method, the coefficient C controlling the saturation speed of kinematic hardening of the yield surface varies depending on stress conditions, whereby the stress-strain relation of the elastic-plastic material is accurately calculated. Furthermore, in the springback-amount prediction method according to the present invention, a computer predicts the springback amount with the stress-strain relation calculated by the stress-strain relation simulation method according to the present invention, and thus the springback amount of the elastic-plastic material during the press forming can be accurately predicted.

Figure 15:
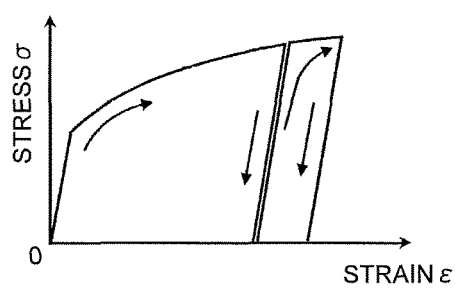
FIG. 15 is a diagram for explaining an effect of the present invention, which is a diagram illustrating one example of a stress-strain relation in a normal-rotation deformation process.
Figure 16:
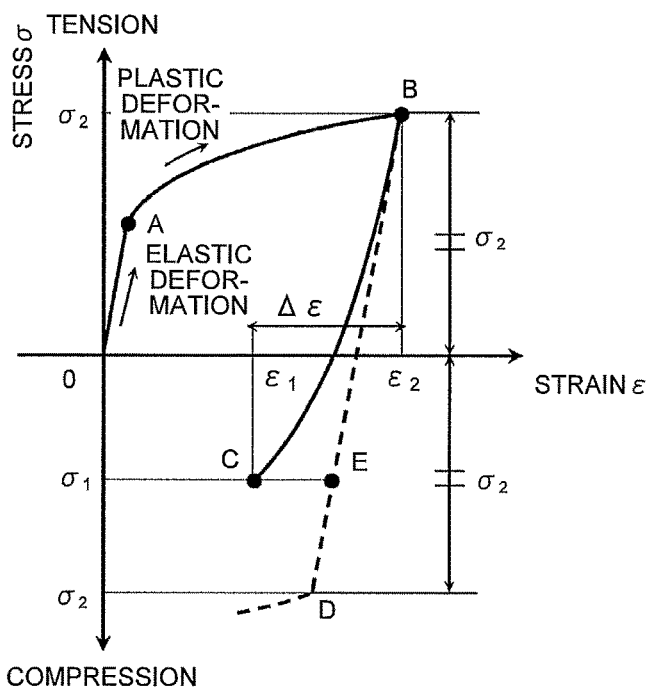
FIG. 16 is an explanatory diagram for explaining a conventional technique.

The method described in Patent Literature 1 studies the expressiveness of the stress-strain relation only when stress is reversed. However, actual press forming may require deformation (normal-rotation deformation) involving a load that is applied in the same direction again after unloading as depicted in FIG. 15. Accordingly, in the conventional method described in Patent Literature 1, the prediction accuracy for the stress-strain relation and the springback amount in the press forming including the normal-rotation deformation may decrease. By contrast, in the present invention, experimental values of the stress-strain relation of the elastic-plastic material obtained by a tension→unloading→re-tension test are also used to determine the material constants of the elastic-plastic constitutive model. Accordingly, the stress-strain relation and also the springback amount in the press forming including the normal-rotation deformation can be accurately predicted.

INDUSTRIAL APPLICABILITY

The present invention is applicable to processing for evaluating a stress-strain relation of an elastic-plastic material. This enables the stress-strain relation of the elastic-plastic material to be accurately simulated.

REFERENCE SIGNS LIST

1 SPRINGBACK ANALYZER
3 DISPLAY DEVICE
5 INPUT DEVICE
7 MAIN MEMORY
9 AUXILIARY STORAGE
11 ARITHMETIC PROCESSING UNIT
13 PRESS-FORMING ANALYSIS UNIT
15 SPRINGBACK ANALYSIS UNIT
21 PUNCH
23 DIE
25 PAD
27 STEEL SHEET

The invention claimed is:

1. A springback-amount prediction method comprising: determining a spring-back amount of a press-formed product including:
(i) an experimental-value acquisition step of plastically deforming an elastic-plastic material to acquire experimental values of a stress-strain relation;
(ii) a first material-constant identification step of, by a computer, with a kinematic-hardening incremental vector $d\alpha_{ij}$ of a yield surface in an elastic-plastic constitutive model as Equation (1), the elastic-plastic constitutive model being defined as a function of stress and back stress, identifying material constants contained in the elastic-plastic constitutive model using the experimental values acquired at the experimental-value acquisition step;
(iii) a second material-constant identification step of, by the computer, based on the Equation (1) into which the material constants identified at the first material-constant identification step are substituted and based on the experimental values acquired at the experimental-value acquisition step, identifying material constants contained in Equation (2); and
(iv) a step of, by the computer, predicting the springback amount with the Equation (1) and the Equation (2) into which the material constants identified are substituted, and the elastic-plastic constitutive model,
modifying a die based upon the determined spring-back amount, and
pressing the die onto a metal sheet to produce the press-formed product,
wherein Equation (1) is defined as follows:

$$d\alpha_{ij} = \left[C\left(\frac{a}{Y}\right)(\sigma_{ij} - \alpha_{ij}) - C_0\rho X_{ij}\right]d\varepsilon^p_{eq}$$

Equation (2) is defined as follows:

$$C = C_a + C_c \exp\left(-\frac{X^n_{eq}}{A}\right)$$

where:
a: maximum value of movement of yield surface
Y: yield stress
$\alpha_{ij}$: movement vector of yield surface
$\sigma_{ij}$: stress vector
$X_{ij}$: yield—surface kinematic—hardening amount after stress reversal
$X_{eq}$: equivalent value of $X_{ij}$
$d\varepsilon^p_{eq}$: equivalent plastic—strain increment
$C_0$, $C_C$, A, n: material constants
$\rho$: variable such that $\rho=1$ or ½.

2. The springback-amount prediction method according to claim 1, wherein variables $X_{ij}$, $\rho$, A, and n in the Equations (1) and (2) are represented by Equation (3), wherein Equation (3) is defined as follows:

$$\begin{array}{l}\text{If } \sigma_{eq} \geq \sigma_{eqmax}, \sigma_{eq} = \sigma_{eq\,max} \\ \quad X_{ij} = \alpha_{ij}, \rho = 1, A = A_1, n = n_1 \\ \text{If } \sigma_{eq} < \sigma_{eq\,max} \\ \quad X_{ij} = \alpha^{tmp}_{ij} - \alpha_{ij}, \rho = \frac{1}{2}, A = A_2, n = n_2\end{array}$$

where
$\sigma_{eqmax}$: maximum value of equivalent stress when isotropic hardening is assumed
$\alpha^{tmp}_{ij}$: back stress at the time of stress reversal
$A_1$, $A_2$, $n_1$, $n_2$: material constants.

3. The springback-amount prediction method according to claim 2, wherein:
as a method for applying plastic deformation to the elastic-plastic material at the experimental-value acquisition step, one method is used out of:
a method in which stress is applied to the elastic-plastic material in a tensile direction to deform the elastic-plastic material plastically and is then unloaded;
a method in which stress is applied to the elastic-plastic material in the tensile direction to deform the elastic-plastic material plastically and is then unloaded, and stress is applied in a compression direction to deform the elastic-plastic material plastically; and a method in which stress is applied to the elastic-plastic material in the tensile direction to deform the elastic-plastic material plastically and is then unloaded, and stress is applied again to the elastic-plastic material in the tensile direction to deform the elastic-plastic material plastically.

4. The springback-amount prediction method according to claim 1, wherein:

as a method for applying plastic deformation to the elastic-plastic material at the experimental-value acquisition step, one method is used out of:

a method in which stress is applied to the elastic-plastic material in a tensile direction to deform the elastic-plastic material plastically and is then unloaded;

a method in which stress is applied to the elastic-plastic material in the tensile direction to deform the elastic-plastic material plastically and is then unloaded, and stress is applied in a compression direction to deform the elastic-plastic material plastically; and a method in which stress is applied to the elastic-plastic material in the tensile direction to deform the elastic-plastic material plastically and is then unloaded, and stress is applied again to the elastic-plastic material in the tensile direction to deform the elastic-plastic material plastically.

5. A manufacturing method comprising:

using a springback analyzer to determine a spring-back amount of a press-formed product, the springback analyzer including:

(i) a press-forming analysis unit that performs press-forming analysis to acquire shape, residual-stress distribution, and strain distribution of the press-formed product through analysis before die release; and (ii) a springback analysis unit that performs springback analysis based on the shape, the residual-stress distribution, and the strain distribution of the press-formed product to acquire the springback amount of the press-formed product after die release, wherein a kinematic-hardening incremental vector $d\alpha_{ij}$ of a yield surface in an elastic-plastic constitutive model that the press-forming analysis unit and the springback analysis unit have is represented by Equations (1) and (2), modifying a die based upon the determined spring-back amount, and pressing the die onto a metal sheet to produce the press-formed product, wherein Equation (1) is defined as follows:

$$d\alpha_{ij} = \left[ C\left(\frac{a}{Y}\right)(\sigma_{ij} - \alpha_{ij}) - C_0 \rho X_{ij} \right] d\varepsilon^p_{eq}$$

Equation (2) is defined as follows:

$$C = C_a + C_c \exp\left(-\frac{X^n_{eq}}{A}\right)$$

where:
- a: maximum value of movement of yield surface
- Y: yield stress
- $\alpha_{ij}$: movement vector of yield surface
- $\sigma_{ij}$: stress vector
- $X_{ij}$: yield—surface kinematic—hardening amount after stress reversal
- $X_{eq}$: equivalent value of $X_{ij}$
- $d\varepsilon^p_{eq}$: equivalent plastic—strain increment
- $C_0$, $C_C$, A, n: material constants
- $\rho$: variable such that $\rho=1$ or ½.

6. The manufacturing method according to claim 5, wherein variables $X_{ij}$, $\rho$, A, and n in the Equations (1) and (2) are represented by Equation (3), wherein Equation (3) is defined as follows:

$$\begin{aligned} &\text{If } \sigma_{eq} \geq \sigma_{eqmax}, \sigma_{eq} = \sigma_{eq\,max} \\ &\quad X_{ij} = \alpha_{ij}, \rho = 1, A = A_1, n = n_1 \\ &\text{If } \sigma_{eq} < \sigma_{eq\,max} \\ &\quad X_{ij} = \alpha^{tmp}_{ij} - \alpha_{ij}, \rho = \frac{1}{2}, A = A_2, n = n_2 \end{aligned}$$

where
- $\sigma_{eqmax}$: maximum value of equivalent stress when isotropic hardening is assumed
- $\alpha^{tmp}_{ij}$: back stress at the time of stress reversal
- $A_1$, $A_2$, $n_1$, $n_2$: material constants.

* * * * *